United States Patent [19]

Jakobson et al.

[11] Patent Number: 5,264,460
[45] Date of Patent: Nov. 23, 1993

[54] PROCESS FOR PREPARING NONIONIC SURFACTANTS

[75] Inventors: Gerald Jakobson; Werner Siemanowski, both of Rheinberg; Karl-Heinz Uhlig, Krefeld-Traar, all of Fed. Rep. of Germany

[73] Assignee: Deutsche Solvay-Werke GmbH, Solingen, Fed. Rep. of Germany

[21] Appl. No.: 824,292

[22] Filed: Jan. 23, 1992

Related U.S. Application Data

[62] Division of Ser. No. 357,607, May 26, 1989, Pat. No. 5,093,043.

[30] Foreign Application Priority Data

May 30, 1988 [DE] Fed. Rep. of Germany ....... 3818293

[51] Int. Cl.$^5$ .................. A61K 7/48; A61K 47/14; C09F 5/08; C09F 7/10
[52] U.S. Cl. ................. 514/786; 514/785; 514/844; 514/847; 514/938; 252/351; 554/148; 554/213; 554/219; 554/223; 554/227
[58] Field of Search ............. 568/728; 514/785, 938, 514/786, 844, 847; 260/407, 410.6, 410.7, 410.8, 415, 416, 419, 427, 428; 554/148, 213, 219, 223, 227; 252/351

[56] References Cited

U.S. PATENT DOCUMENTS

| | | | |
|---|---|---|---|
| 2,022,766 | 12/1935 | Harris | 514/938 |
| 3,936,391 | 2/1976 | Gabby et al. | 252/356 |
| 4,035,513 | 7/1977 | Kumano | 514/785 |
| 4,454,113 | 6/1984 | Hemker | 514/786 |
| 4,539,266 | 9/1985 | Miyazaki | 428/900 |
| 4,971,721 | 11/1990 | Takahashi et al. | 514/844 |

FOREIGN PATENT DOCUMENTS

| | | | |
|---|---|---|---|
| 0070535 | 1/1983 | European Pat. Off. | |
| 1808229 | 7/1969 | Fed. Rep. of Germany | |
| 31037 | 3/1980 | Japan | 514/786 |
| 193928 | 10/1985 | Japan | 514/785 |

OTHER PUBLICATIONS

Soviet Inventions Illustrated, Section Ch., Week D18, SU 759-503, Tula Chem. Ind. Res.
Chemical Abstract, vol. 41, pp. 2391-2394 (1947).

*Primary Examiner*—Jeffrey E. Russel
*Attorney, Agent, or Firm*—Foley & Lardner

[57] ABSTRACT

A process for preparing a nonionic surfactant includes the steps of: cleaving at least one of the isopropylidene groups of an isopropylidene polyglycerol $C_6$-$C_{22}$-fatty acid or mono- or polyhydroxy fatty acid ester, by hydrolysis or ketal exchange, in the presence of acid, at a temperature in the range of about 20° C. to about 100° C., and at atmospheric, reduced or superatmospheric pressure, thereby regenerating hydroxyl groups on the polyglycerol; and recovering the resultant polyol ester nonionic surfactant. Such polyol ester surfactants are useful as emulsifiers, especially for preparing skin care or cosmetic formulations and paints and wood-preservation agents.

17 Claims, No Drawings

PROCESS FOR PREPARING NONIONIC SURFACTANTS

This application is a division of application Ser. No. 07/357,607, filed May 26, 1989, now U.S. Pat. No. 5,093,043.

BACKGROUND OF THE INVENTION

The present invention relates to a process for preparing fatty acid or mono- or polyhydroxy fatty acid esters of polyglycerols from intermediate fatty acid or mono- or polyhydroxy fatty acid esters of isopropylidene derivatives of polyglycerols, in which specific process conditions for the preparation of the fatty acid esters of polyglycerol must be followed.

The invention further relates to the use of the fatty acid esters of polyglycerol prepared by such process as nonionic surfactants, and to skin care and/or cosmetic formulations or ointments, paints and wood-protection agents, in which at least one such nonionic surfactant is used as an emulsifier.

It is already known to prepare fatty acid esters, for example tetraesters, of polyglycerols by heating diglycerol for several days with a large excess of fatty acids, e.g., lauric, palmitic, stearic or oleic acid, but such esters are generally obtained in the form of brown solid or oily compounds (see, e.g., C.A., 41, 2392 (1947)). As a result of the long heating, only heavily contaminated products can be obtained in very poor yields. The tetraesters thus prepared cannot be used as surfactants. The attempt has therefore been made to obtain the corresponding compounds from isopropylidenediglycerol and stearyl chloride in chloroform. However, the required amount of work involved is considerable, since after the reaction the mixture solidifies to give a paste, which must be taken up after 36 hours in benzene. After the aqueous solution is separated off and the organic phase is washed with water, excess stearic acid must be removed by extraction with 10% sodium bicarbonate solution, the organic phase must be dried over sodium sulfate, and the solvent must be distilled off. The resulting residue has to be recrystallized two or several times with alcohols. A further disadvantage of this process is that hydrochlorides are formed in molar ratios, which either have to be processed further or represent polluting substances.

OBJECTS OF THE INVENTION

One object of the present invention is to provide an improved process for preparing nonionic surfactants, in particular fatty acid esters of polyglycerols, from lower alkyl fatty acid or mono- or polyhydroxy fatty acid esters.

Another object of the invention is to provide a process for preparing fatty acid esters of polyglycerols which makes it possible to carry out selective esterifications of polyglycerols on a large industrial scale.

Another object of the invention is to provide a process for preparing fatty acid esters of polyglycerols wherein unreacted reagents or reaction byproducts can be at least partially recycled.

Another object of the invention is to provide substantially pure vicinal fatty acid diesters of diglycerol, fatty acid monoesters of the central hydroxyl group of triglycerol, and fatty acid monoesters and diesters of one or both of the central hydroxyl groups of tetraglycerol.

Another object of the invention is to provide nonionic surfactants that are useful to prepare both water-in-oil and oil-in-water emulsions with high water content and good stability over time.

SUMMARY OF THE INVENTION

These and other objects of the invention are achieved by providing a process for preparing a nonionic surfactant, which comprises the steps of:

(a) cleaving at least one of the isopropylidene groups of an isopropylidene polyglycerol $C_6$–$C_{22}$-fatty acid or mono- or polyhydroxy fatty acid ester, by hydrolysis or ketal exchange, in the presence of acid, at a temperature in the range of about 20° C. to about 100° C., and at atmospheric, reduced or superatmospheric pressure, thereby regenerating hydroxyl groups on the polyglycerol; and (d) recovering the resultant polyol ester nonionic surfactant.

The invention further includes improved methods of preparing emulsions using the nonionic surfactants prepared by the foregoing process as emulsifiers. Also provided are skin care and cosmetic formulations, paints and wood-protection agents incorporating the nonionic surfactants according to the invention as emulsifiers.

DETAILED DESCRIPTION

According to the invention, a process is provided for the preparation of fatty acid or mono- or polyhydroxy fatty acid esters of polyglycerols. Hereinafter, the term "fatty acid ester" will include esters of non-hydroxylated, monohydroxylated and/or polyhydroxylated fatty acids unless otherwise explicitly indicated. Alkyl fatty acid esters having $C_6$–$C_{22}$ in the fatty acid component and $C_1$–$C_4$ in the alkyl component are first reacted in alkaline medium with one or more isopropylidene derivatives of a polyglycerol to form isopropylidene polyglycerol fatty acid esters.

Reaction conditions for producing the intermediate fatty acid esters of isopropylidene polyglycerols are disclosed and claimed in copending and commonly assigned U.S. patent application Ser. No. 07/357,006 Jakobson et al., filed on even date herewith, now U.S. Pat. No. 5,024,781 and corresponding to German P 38 18 292.0, filed May 30, 1988, which is incorporated herein in its entirety by reference.

The reaction is carried out at temperatures of 140° C.–220° C., preferably 170° C.–200° C., and in a vacuum of 950–5 mbar, preferably 500–10 mbar, and the $C_1$–$C_4$ alcohol which is formed is removed by distillation, preferably removed continuously, and the resultant reaction product is recovered, preferably purified by filtration, centrifugation, distillation and/or fractional distillation. At least one isopropylidene group of the reaction product is then cleaved by hydrolysis or alcoholysis, at 20°–100° C., preferably 50° C.–80° C., and at atmospheric, reduced or super-atmospheric pressure, in the presence of acid.

Suitable alkyl fatty acid esters include, e.g., saturated or unsaturated, branched or unbranched alkyl fatty acid esters, including esters of forerun $C_6$–$C_{10}$ fatty acids, lauric acid, myristic acid, coconut fatty acid, stearic acid, behenic acid and/or 2-ethylhexanoic acid, isostearic acid, palm oil fatty acid, oil fatty acid, soya oil fatty acid and linoleic acid.

Suitable alkyl hydroxy fatty acid esters include, e.g., ethyl 12-hydroxystearate and alkyl ricinoleic acid esters, to name a few that are readily available commercially.

The isopropylidene derivatives of polyglycerol which are preferably used are mono- and/or diisopropylidene derivatives of di-, tri- and/or tetraglycerol (with the exception of diisopropylidene-diglycerol).

The reaction product is preferably separated after the transesterification from insoluble components by filtration at temperatures of 20° C.-100° C., preferably 40° C.-70° C.

According to a preferred embodiment, after the reaction of the alkyl fatty acid ester, alkyl mono- and/or polyhydroxy fatty acid ester with one or more mono- or diisopropylidene derivatives of di-, tri- and/or tetraglycerol (with the exception of diisopropylidenediglycerol) the excess of the unconverted alkyl fatty acid ester, alkyl mono- and/or polyhydroxy fatty acid ester and/or of the unconverted iso- or diisopropylidene derivatives of di-, tri- and/or tetraglycerol is distilled off in vacuo, preferably distilled off continuously.

The remaining reaction product, largely fatty acid esters of isopropylidene polyglycerol, is suspended in an anhydrous or aqueous lower ($C_1C_6$, preferably $C_2-C_4$) alcohol, and at least one of the isopropylidene protecting groups is cleaved by hydrolysis and/or alcoholysis, at 20° C.-100° C., preferably 50° C.-80° C., in the presence of an acid catalyst. After the reaction is completed, the solvent mixture formed (water, acetone formed, alcohol, acetone-$C_1$-$C_6$-alcohol ketal) is distilled off.

Suitable acids include any strong acid, e.g., mineral acids, organic acids, strongly acidic ion exchange resins, and the like, preferably, mineral acids such as sulfuric acid, phosphoric acid and the like. The pH of the isopropylidene cleavage reaction is advantageously in the range of about 1-6, preferably about 2-4, especially about pH 3.

The lower alcohol which is used is preferably n-butanol.

The amount of water added to the alcohol, if any, is advantageously 1-5 mole per isopropylidene group, preferably 1.1-3.5 mole per isopropylidene group.

Before the solvent is distilled off, it is preferred to neutralize and/or remove the acid present in the reaction mixture or the acid catalyst and/or to distill off the solvent mixture. Neutralization can be effected using any conventional base. According to a preferred embodiment, the neutralization is carried out by addition of a basic anion exchange resin, especially a resin charged with hydroxide ions, and the anion exchange resin is subsequently filtered off.

The invention furthermore relates to the use of certain nonionic polyglycerol fatty acid ester surfactants, which are preferably prepared by the process according to the invention, as water-in-oil emulsifiers, preferably consisting of at least one vicinal diester of diglycerol or using them in addition to other surfactants. Vicinal diesters of diglycerol are prepared according to the invention from fatty acid diesters of the mono-isopropylidene derivative of diglycerol, prepared under conditions which favor formation of the diester (as disclosed in the companion application incorporated by reference herein), by cleavage of the isopropylidene group.

The invention furthermore relates to the use of certain nonionic polyglycerol fatty acid ester surfactants, which are preferably prepared by the process according to the invention, as oil-in-water emulsifiers, preferably in the form of the central monoesters of triglycerol and/or the central mono- and/or diesters of tetraglycerol. Such esters are prepared according to the invention from diisopropylidene derivatives of triglycerol or tetraglycerol, both of which have a free hydroxyl group on the central glycerol(s) which can be esterified, after which one or both of the isopropylidene groups is/are cleaved.

The use of the surfactants refers preferably to their use as additives, wetting agents, dispersants, solubilizing agents, solvents and emulsifiers for skin protection agents and skin care oils, lubricants, textile auxiliary agents, food, detergents and cleaning agents, disinfectants, for biocides, dyes and paints, wood-preservation agents and for pharmaceutical and/or cosmetic formulations.

According to a preferred embodiment, the vicinal diesters of diglycerol which have a diglycerol monoester content of 0.01–40% by weight, preferably 7–25% by weight, (relative to 100 parts by weight of the vicinal diester of diglycerol) are used as surfactants, preferably as water-in-oil emulsifiers, in skin care or cosmetic formulations.

The invention furthermore relates to skin care and/or cosmetic formulations using at least one nonionic surfactant and water and, if appropriate, at least one conventional auxiliary, processing agent, consistency-improving agent, stabilizing agent and/or preservative and, if appropriate, at least one conventional fat, wax, oil and/or a fat-like substance and/or a perfume, wherein the skin care preparation or cosmetic formulation is (a) an oil-in-water (O/W) emulsion, containing 30–95% by weight of water, preferably 50–88% by weight, the nonionic surfactant being at least one of a surfactant based on a di-, tri- and/or tetraglycerol fatty acid ester, e.g a di- tri- or tetraglycerol $C_6$-$C_{22}$-fatty acid or mono- or polyhydroxy fatty acid ester, present as emulsifying agent in an amount of 0.5–10% by weight, preferably 1–6.5% by weight (relative to 100 parts by weight of the skin care and/or cosmetic formulation); or (b) a water-in-oil (W/O) emulsion, containing 20–90% by weight of water, preferably 70–88% weight, the nonionic surfactant being a vicinal $C_6$-$C_{22}$-fatty acid or mono- or polyhydroxy fatty acid diester of diglycerol.

The skin care and/or cosmetic or medicinal formulation according to the invention, which uses the nonionic surfactant (W/O creams and lotions), leads to occlusive hydration as a result of its occlusive effect on the skin, that is to say, it produces the effect of a humidity chamber by virtue of a sealing film covering the skin. Water from the emulsion penetrates into the horny layer lying below. The skin is protected by the lipid film covering it against evaporation. Polyglycerol esters are specifically suitable as emulsifiers for the preparation of this type of W/O emulsion, due to their very good dermatological and toxicological properties.

It is known that a W/O emulsion is formed upon reduction of the interfacial tension to <5 mN/m and formation of a contact angle between oil and water of >90°. For this, maximum surface tension of the aqueous phase is required. However, water-soluble components in the emulsifier such as diglycerol monoesters and/or higher polyglycerol esters would reduce the surface tension after diffusion into the aqueous phase, that is to say, diminish the contact angle to <90°. This means that the W/O emulsion becomes unstable by partial phase reversal to O/W.

It has now been found that the diglycerol di(fatty acid esters) prepared according to the invention, i.e., substantially pure vicinal diglycerol diesters, and having a defined degree of hydrophilicity (and the formulations prepared therefrom) do not have these disadvantages.

A convenient measure of hydrophilicity for these surfactants is the HLB Value by Griffin.

The vicinal diglycerol di(fatty acid esters) according to the invention which are especially advantageous for forming W/O emulsions with high water content have a hydrophilicity according to the foregoing measurement system of 4.36, preferably 4–4.6.

The different content of water-soluble components in the emulsifier of the product according to the invention compared to that of a commercially available product may be illustrated by the following example:

Both products were suspended at 1% strength in water at 70° C., cooled and filtered.

| Surface tension measured in the filtrate: | |
|---|---|
| diglycerol diisostearate according to the invention | 46 mN/m |
| commercial polyglycerol diisostearate | 34 mN/m |

However, a drop of the surface tension to 34 mN/m is already in the region of most O/W emulsifiers.

The commercial polygylcerol diisostearate has the approximate composition: polyglycerol condensed from glycerol with approximately two units of glycerol esterified with two moles of isostearic acid.

Using the diglycerol diisostearate according to the invention, it is possible to develop stable W/O emulsions, for example for moisture creams and lotions and also for medicinal purposes. Using substantially pure vicinal diglycerol di(fatty acid esters), it is possible to prepare stable W/O emulsions having a water content of up to 82%.

Another preferred embodiment is a cream which contains 30–90 parts by weight, preferably 50–88 parts by weight of water; 0.5–25 parts by weight, preferably 1–6.5 parts by weight, of the surfactant or surfactant mixture according to the invention or of a mixture of the surfactant according to the invention with another surfactant; and optionally, 0–30 parts by weight, preferably 0.1–25 parts by weight, of at least one thickening agent, animal and/or vegetable oil, mineral oil, synthetic oil or wax; 0–14.95 parts by weight, preferably 2–14.9 parts by weight, of an organic solvent; 0.05–40 parts by weight, preferably 4.1–8.9 parts by weight, of at least one active compound in the form of at least one skin care active compound, pharmaceutical active compound, local-anesthetic active compound, disinfectant active compound; and/or a perfume or an aromatic substance.

In the foregoing cream, the surfactant is preferably diglycerol diisostearate.

The other surfactants that can be used in combination therewith in a surfactant mixture include, e.g., diglycerol dioleate.

Advantageously, the amount of the surfactant according to the invention in such surfactant mixture is at least about 4.5% by weight, preferably about 3.2% by weight, more preferably about 1–1.5% by weight.

The invention furthermore relates to a paint or wood-protection agent containing at least one binder or binder mixture and a liquid emulsion as the main constituent, said emulsion comprising an organic solvent or solvent mixture, preferably also using a water-insoluble organic, highly volatile solvent or solvent mixture, and water, and containing as a nonionic surfactant emulsifier 0.01–10% by weight, preferably 0.1–5% by weight, of at least one of a di-, tri- or tetraglycerol $C_6$–$C_{22}$-fatty acid or mono- or polyhydroxy fatty acid ester or a vicinal $C_6$–$C_{22}$ fatty acid or mono- or polyhydroxy fatty acid diester of diglycerol, and further comprising at least one of a pigment or pigment mixture, a filler or filler mixture, a dye, and where appropriate a processing aid, a siccative or a biocide.

PREPARATIVE EXAMPLES

1.1 Reaction of methyl oleate with diisopropylidinetriglycerol 1.52 kg (5 mol) of methyl oleate and 25 g (0.2 mol) of potassium carbonate are placed in a 4 l g flask and heated with stirring to about 160° C. At a reduced pressure of about 100 mbar, small amounts of water which may be present are distilled off. 820 g (2.5 mol) of diisopropylidenetriglycerol are then added, and the reaction temperature is increased to 180° C.–190° C. At 400–50 mbar, the methanol formed is removed by distillation. After a reaction time of 4–5 hours, the mixture is cooled to about 70° C., and precipitated components are filtered off.

Excess alkyl fatty acid ester and unconverted diisopropylidenetriglycerol are removed by distillation at $\leq 0.4$ mbar and a column head temperature of about 160° C. The remaining crude product is then fine-distilled in a short-path evaporation apparatus at $\leq 0.1$ mbar and an oil flow temperature of 210° C.

1.2 Hydrolysis of diisopropylidenetriglycerol monooleate to triglycerol monooleate 2.5 kg (about 4.4 mol) of diisopropylidenetriglycerol monooleate, prepared by the process described in Preparative Example 1.1, are added to a mixture of 250 ml of water and 2.0 l of n-butanol. The reaction solution is adjusted to a pH of about 3 by means of 1-molar sulfuric acid, heated to 70° C., and stirred for 4–5 hours. After the reaction is completed, $OH^-$-charged anion exchanger is added to the mixture until the reaction solution is neutral.

The ion exchanger is filtered off, the filtrate, if necessary, is decolorized by means of activated carbon, and the low-boiling components (n-butanol, water, acetone formed) are distilled off in vacuo.

2.1 Reaction of methyl palmitate with monoisopropylidenediolycerol 300 g (about 1 mol) of methyl palmitate and 0.5 g of lithium hydroxide monohydrate are placed in a 2 l flask and heated with stirring to 160° C. At 150 mbar, the water (from the catalyst and that introduced by the fatty acid ester) is removed by distillation.

1.031 kg (5 mol) of monoisopropylidenediglycerol are then added, and the reaction temperature is increased to 190° C. At 400–50 mbar (lower pressure toward the end of the reaction), the methanol formed is removed by distillation. After a reaction time of 3 hours, the mixture is cooled to 45° C., and precipitated components are filtered off.

Excess monoisopropylidenediglycerol is removed by distillation at $\leq 0.2$ mbar and an oil flow temperature of about 140° C. in a short-path evaporation apparatus, the remaining crude product is finally fine-distilled in the same apparatus at $\leq 0.2$ mbar and an oil flow temperature of 205° C.

2.2 Hydrolysis of monoisopropylidenediglycerol monopalmitate to diglycerol monopalmitate 1.5 kg of monoisopropylidenediglycerol monopalmitate, prepared according to the process of Preparative Example 2.1, are added to a mixture of 200 ml of water and 2.0 l of n-butanol. The reaction solution is adjusted to a pH of about 3 by means of 1-molar sulfuric acid, heated to 70° C., and stirred for 4–5 hours. After the reaction is completed, $OH^-$-charged anion exchanger is added to the mixture until the reaction solution is neutral.

The ion exchanger is filtered off, the filtrate, if necessary, is decolorized by means of activated carbon, and the low-boiling components (n-butanol, water, acetone formed) are distilled off in vacuo.

FORMULATION EXAMPLES

1 Moisture cream (W/O type):
2.5% of diglycerol diisostearate according to the invention
5.0% of paraffin oil, viscous
5.0% of decyl oleate (Cetiol V, Henkel)
0.7% of Mg stearate
0.3% of Al stearate
4.0% of diglycerol
0.3% of magnesium sulfate heptahydrate
0.1% of Rokonsal CI (Biochema Schwaben)
0.3% of perfume
81.8% of water fully deionized The formulation is prepared in conventional fashion, as noted above, and the formulation and preparation are duplicated, except for using as a substitute for the diglycerol diisostearate according to the invention two commercially available polyglycerol fatty acid ester mixtures of the same HLB value.

Commercial product 1 has the composition oleic acid polyglycerol ester.

Commercial product 2 has the composition isostearic acid polygylcerol ester.

All samples are subjected to conventional storage at 40° C. in a heating cabinet. The stabilities of the formulations are as follows:

| Formulation containing: | storage at 40° C.: |
| --- | --- |
| Diglycerol diisostearate according to the invention | stability >3 months |
| Commercial product 1 | unstable after 12 days |
| Commercial product 2 | unstable after 18 days |

2. Skin care cream (W/O type):
4.5% of diglycerol diisostearate according to the invention
6.0% of isopropyl myristate
3.5% of Miglyol 812 neutral oil (Troisdorf-Huels)
6.0% of paraffin oil, viscous
3.0% of vaseline white
4.0% of microwax (Lunacera MW, Fuller)
0.3% of magnesium sulfate heptahydrate
0.1% of Rokonsal CI
0.3% of perfume
72.3% of water fully deionized The formulation is prepared as in Formulation Example 1, as are the duplicate formulations using the same commercially available products and tested for stability at 40° C.

| Recipe containing: | storage at 40° C.: |
| --- | --- |
| Diglycerol diisostearate according to the invention | stability >3 months |
| Commercial product 1 | unstable after 8 days |
| Commercial product 2 | unstable after 23 days |

3. Skin cream (O/W type)
1.5% of triglycerol monoisostearate according to the invention
12.0% of glycerol mono-/distearate
2.0% of cetyl alcohol
5.0% of Cetiol SN (Henkel)
3.0% of acetylated lanolin
10.0% of diglycerol
10.0% of glycerol
0.12% of Carbopol 940 (BF Goodrich)
0.1% of preservative
0.2% of perfume
0.2% of neutralizing agent
55.88% of water fully deionized Stability in the storage test at 40° C.: >6 months.

The foregoing description has been set forth merely to describe illustrative embodiments of the invention and is not intended to be limiting. Since modifications of the described embodiments incorporating the spirit may occur to those skilled in the art, the scope of the invention should be limited solely with respect to the appended claims and equivalents.

What is claimed is:

1. In a process for preparing a water-in-oil emulsion, wherein an aqueous phase and an oily phase are emulsified, in the presence of an emulsifier, the improvement comprising the step of carrying out said emulsification in the presence of an emulsifier which comprises an effective emulsifying amount of a nonionic surfactant prepared by a process which comprises the steps of:

(a) cleaving at least one of the isopropylidene groups of a vicinal $C_6$–$C_{22}$-fatty acid or mono- or polyhydroxy fatty acid diester of isopropylidene diglycerol, by hydrolysis or ketal exchange, in the presence of acid, at a temperature in the range of about 20° C. to about 100° C., and at atmospheric, reduced or superatmospheric pressure, thereby regenerating hydroxyl groups on the diglycerol; and (b) recovering as the resultant nonionic surfactant a substantially pure vicinal diester of diglycerol containing 0.01–40% by weight of diglycerol monoester.

2. The process of claim 1, wherein said water-in-oil emulsion contains 20–90% by weight of water.

3. The process of claim 1, wherein said water-in-oil emulsion contains 70–88% by weight of water.

4. The process of claim 2, wherein said water-in-oil emulsion is a skin care or cosmetic formulation.

5. The process of claim 4, wherein said water-in-oil emulsion further comprises one or more ingredients for skin care or cosmetic formulations, selected from the group consisting of an auxiliary, a processing agent, a consistency-improving agent, a stabilizing agent, a preservative, a fat, a wax, an oil, and a perfume.

6. The process of claim 4, wherein said water-in-oil emulsion further comprises a hydrophobic substance.

7. The process of claim 6, wherein said hydrophobic substance is paraffin oil, a petroleum jelly, acetylated lanolin or a microwax.

8. In a process for preparing a water-in-oil emulsion, wherein an aqueous phase and an oily phase are emulsified, in the presence of an emulsifier, the improvement comprising the step of carrying out said emulsification in the presence of an emulsifier which comprises an effective emulsifying amount of a nonionic surfactant prepared by a process which comprises the steps of:
  (a) cleaving at least one of the isopropylidene groups of a $C_6$–$C_{22}$-fatty acid or mono- or polyhydroxy fatty acid monoester, diester or mixture of monoester and diester of diisopropylidene tetraglycerol, by hydrolysis or ketal exchange, in the presence of acid, at a temperature in the range of about 20° C. to about 100° C., and at atmospheric, reduced or superatmospheric pressure, thereby regenerating hydroxyl groups on the tetraglycerol; and
  (b) recovering as the resultant nonionic surfactant substantially pure monoester, diester or mixture of monoester and diester of tetraglycerol, the esters being substantially only on the central glycerol moieties thereof.

9. The process of claim 8, wherein said oil-in-water emulsion contains 30–95% by weight of water.

10. The process of claim 9, wherein said oil-in-water emulsion contains 50–80% by weight of water.

11. The process of claim 9, wherein said oil-in-water emulsion is a skin care or cosmetic formulation.

12. The process of claim 11, wherein said oil-in-water emulsion further comprises one or more ingredients for skin care or cosmetic formulations, selected from the group consisting of an auxiliary, a processing agent, a consistency-improving agent, a stabilizing agent, a preservative, a fat, a wax, an oil, and a perfume.

13. The process of claim 11, wherein said oil-in-water emulsion further comprises a hydrophobic substance.

14. The process of claim 13, wherein said hydrophobic substance is paraffin oil, a petroleum jelly, acetylated lanolin or a microwax.

15. A skin care preparation or cosmetic formulation, comprising at least one nonionic surfactant and water, and further comprising one or more ingredients for skin care or cosmetic formulations, selected from the group consisting of an auxiliary, a processing agent, a consistency-improving agent, a stabilizing agent, a preservative, a fat, a wax, an oil, and a perfume; and wherein said skin care preparation or cosmetic formulation is
  a water-in-oil emulsion, containing 70–88% by weight of water, wherein said nonionic surfactant is a vicinal $C_6$–$C_{22}$-fatty acid or mono- or polyhydroxy fatty acid diester of diglycerol.

16. A skin care preparation or cosmetic formulation, comprising at least one nonionic surfactant and water, and further comprising a hydrophobic substance; and wherein said skin care preparation or cosmetic formulation is a water-in-oil emulsion, containing 70–88% by weight of water, wherein said nonionic surfactant is a vicinal $C_6$–$C_{22}$-fatty acid or mono- or polyhydroxy fatty acid diester of diglycerol.

17. The skin care preparation or cosmetic formulation of claim 16, wherein said hydrophobic substance is paraffin oil, a petroleum jelly, acetylated lanolin or a microwax.

* * * * *